United States Patent
Landolina et al.

(10) Patent No.: US 12,016,968 B2
(45) Date of Patent: Jun. 25, 2024

(54) HIGHLY EFFICACIOUS HEMOSTATIC ADHESIVE POLYMER SCAFFOLD

(71) Applicant: Cresilon, Inc., Brooklyn, NY (US)

(72) Inventors: Joseph A. Landolina, Brooklyn, NY (US); Omar M. Ahmad, Brooklyn, NY (US)

(73) Assignee: Cresilon, Inc., Brooklyn, NY (US)

( * ) Notice: Subject to any disclaimer, the term of this patent is extended or adjusted under 35 U.S.C. 154(b) by 0 days.

(21) Appl. No.: 17/133,089

(22) Filed: Dec. 23, 2020

(65) Prior Publication Data

US 2021/0322630 A1    Oct. 21, 2021

Related U.S. Application Data (63) Continuation of application No. 15/739,095, filed as application No. PCT/US2015/036894 on Jun. 22, 2015, now abandoned.

(51) Int. Cl.
| | |
|---|---|
| *A61L 26/00* | (2006.01) |
| *A61L 15/22* | (2006.01) |
| *A61L 15/42* | (2006.01) |
| *A61L 15/58* | (2006.01) |
| *A61L 24/00* | (2006.01) |
| *A61L 24/04* | (2006.01) |
| *C08J 3/075* | (2006.01) |

(52) U.S. Cl.
CPC ......... *A61L 26/0052* (2013.01); *A61L 15/225* (2013.01); *A61L 15/42* (2013.01); *A61L 15/58* (2013.01); *A61L 24/001* (2013.01); *A61L 24/043* (2013.01); *A61L 26/0066* (2013.01); *A61L 26/008* (2013.01); *C08J 3/075* (2013.01); *A61L 2300/232* (2013.01); *A61L 2300/236* (2013.01); *A61L 2300/418* (2013.01); *C08J 2305/04* (2013.01); *C08J 2305/08* (2013.01)

(58) Field of Classification Search
None
See application file for complete search history.

(56) References Cited

U.S. PATENT DOCUMENTS

| | | | |
|---|---|---|---|
| 4,524,064 A | 6/1985 | Nambu | |
| 4,956,350 A | 9/1990 | Mosbey | |
| 5,034,324 A | 7/1991 | Shinozaki et al. | |
| 5,670,169 A | 9/1997 | Cornell et al. | |
| 5,836,970 A | 11/1998 | Pandit | |
| 6,150,581 A | 11/2000 | Jiang et al. | |
| 6,200,595 B1 | 3/2001 | Motoyashiki et al. | |
| 6,391,294 B1 | 5/2002 | Dettmar et al. | |
| 6,414,033 B1 | 7/2002 | Sceusa | |
| 7,112,713 B2 | 9/2006 | Sceusa | |
| 9,687,584 B1 | 6/2017 | Landolina | |
| 2002/0032488 A1 | 3/2002 | Brekke et al. | |
| 2003/0206958 A1 | 11/2003 | Cattaneo et al. | |
| 2005/0203058 A1 | 9/2005 | Johnson | |
| 2005/0240137 A1 | 10/2005 | Zhu et al. | |
| 2007/0003510 A1 | 1/2007 | Henry et al. | |
| 2007/0166351 A1 | 7/2007 | Hossainy | |
| 2008/0139694 A1 | 6/2008 | Ratcliffe | |
| 2009/0041858 A1 | 2/2009 | Jensen | |
| 2009/0087469 A1 | 4/2009 | Zhang et al. | |
| 2009/0117175 A1 | 5/2009 | Finkielsztein et al. | |
| 2009/0123509 A1* | 5/2009 | Berkland | A61L 26/008 424/422 |
| 2010/0117266 A1 | 5/2010 | Takakura et al. | |
| 2011/0144229 A1 | 6/2011 | Meyerhoff et al. | |
| 2011/0237539 A1 | 9/2011 | Yang et al. | |
| 2011/0251639 A1 | 10/2011 | Thomas et al. | |
| 2011/0287067 A1 | 11/2011 | Stewart | |
| 2012/0093686 A1* | 4/2012 | Kirsch | A61L 2/14 422/23 |
| 2013/0039822 A1 | 2/2013 | Hasan | |
| 2013/0150883 A1 | 6/2013 | Fette et al. | |
| 2013/0261192 A1 | 10/2013 | Yang et al. | |
| 2013/0316007 A1 | 11/2013 | Ma et al. | |
| 2014/0287061 A1 | 9/2014 | Landolina | |
| 2018/0185543 A1 | 7/2018 | Landolina et al. | |

FOREIGN PATENT DOCUMENTS

| | | |
|---|---|---|
| CA | 2134635 | 5/1995 |
| CN | 1810298 | 8/2006 |
| CN | 101463144 | 6/2009 |
| CN | 101463145 | 6/2009 |
| JP | 59-139310 | 8/1984 |

(Continued)

OTHER PUBLICATIONS

Becker, Journal of Biomedical Materials Research, 54, 2001 (Year: 2001).*
48th Polymer Preprints, Japan 1999, vol. 48, No. 10, pp. 2431-2432.
Abreu et al., "Influence of the composition and preparation method on the morphology and swelling behavior of alginate-chitosan hydrogels." Carbohydrate Polymers, Mar. 2008, 74(2), pp. 283-289.
Abstract from Database WPI XP002738085; Japanese Application No. 2000-545736 (Kuraray Co. Ltd.), Jul. 4, 2000 (2 pgs.).
Abstract from Database WPI XP002738086; Japanese Application No. 2000-357854 (Kuraray Co. Ltd.), Apr. 25, 2000 (1 pg.).
Abu-Jdayil et al., "Modification of the rheological behaviour of sodium alginate by chitosan and multivalent electrolytes", Italian Journal of Food Science, vol. 25, pp. 196-201 (2013). Retrieved from the Internet. <URL: http://www.researchgate.net/profile/Basim_Abu- Jdayil/publication/237866139.

(Continued)

*Primary Examiner* — Robert A Wax
*Assistant Examiner* — William Craigo
(74) *Attorney, Agent, or Firm* — Nelson Mullins Riley & Scarborough LLP; Jane E. Remillard, Esq.; Cynthia L. Kanik (57) ABSTRACT

The invention relates to biocompatible polymer gel compositions useful in facilitating and maintaining hemostasis. The biocompatible polymeric gel composition is comprised of (a) one or more than one polyanionic polymer, (b) one or more than one polycationic polymer, and (c) a solvent. A preferred composition includes sodium alginate, chitosan, and water to produce an adhesive hemostatic device that is useful in facilitating and maintaining rapid hemostasis.

19 Claims, 3 Drawing Sheets

(56) References Cited

FOREIGN PATENT DOCUMENTS

| | | |
|---|---|---|
| JP | 06-319517 | 11/1994 |
| JP | 11-318407 | 11/1999 |
| JP | 2000-116765 | 4/2000 |
| JP | 2000-186048 | 7/2000 |
| JP | 2001-81237 | 3/2001 |
| JP | 2004-041586 | 2/2004 |
| JP | 2008-507362 | 3/2008 |
| JP | 2009-537268 | 10/2009 |
| JP | 2011-218165 | 11/2011 |
| WO | WO-1994/006484 | 3/1994 |
| WO | WO-00/12144 | 3/2000 |
| WO | WO-2004/091592 | 10/2004 |
| WO | WO-2006/005340 | 1/2006 |
| WO | WO-2006/012541 | 2/2006 |
| WO | WO-2007/015761 | 2/2007 |
| WO | WO-2007/135114 | 11/2007 |
| WO | WO-2010/117266 | 10/2010 |
| WO | WO-2011/011658 | 1/2011 |
| WO | WO-2011/075557 | 6/2011 |
| WO | WO-2013/050794 | 4/2013 |
| WO | WO-2013/071235 | 5/2013 |
| WO | WO-2013071235 A1 * 5/2013 ............ A61K 47/30 |
| WO | WO-2014/091312 | 6/2014 |
| WO | WO-2014091312 A2 * 6/2014 ............ A61K 35/54 |
| WO | WO-2014/169111 | 10/2014 |
| WO | WO-2016-209198 | 12/2016 |

OTHER PUBLICATIONS

Becker et al., Calcium alginate gel: A biocompatible and mechanically stable polymer for endovascular embolization, Journal of Biomedical Materials Research, vol. 54, pp. 76-86 (2001).

Belman et al., "From the Battlefield to the Street-Experience of a Suburban Fire/EMS Agency with Chitosan Dressing," 2006, pp. 46-47.

Dai et al., "Chitosan-Alginate Sponge: Preparation and Application in Curcumin Delivery for Dermal Wound Healing in Rat", Journal of Biomedicine and Biotechnology, 2009, vol. 2009, pp. 1-8.

Extended European search opinion for European Application No. 15896492.4 dated Jan. 28, 2019. (8 pages).

Gakkaishi, Sen-I, (Textile and Industry), 1990, vol. 46, No. 12, pp. 576-580.

Gotoh et al., "Preparation of alginate-chitosan hybrid gel beads and adsorption of divalent metal ions," Chemosphere, vol. 55, 2004, pp. 135-140.

He et al., "Study on synergistic interaction and gelation of chitosan and sodium alginate." J. Wuhan Univ. (Nat. Sci. Ed.), Apr. 2002, vol. 48, No. 2, pp. 193-196. (English Abstract only).

Hett et al., Sonoclot analysis. British Journal of Anaesthesia, vol. 75, 1995, pp. 771-776. Retrieved from the Internet. <URL:http://bja.oxfordjournals.org/content/75/6/771.full.pdf>.

Hong et al., "Accelerated wound healing by smad3 antisense oligonucleotides-impregnated chitosan/alginate polyelectrolyte complex". Biomaterials 2008, vol. 29, pp. 4831-4837.

Hou et al., "Studies on the Preparation of Chitosan-sodium Alginate Mixed Gel and Immobilization of Glucoamylase by Embedding Method," Journal of Chinese Institute of Food Science and Technology, 2009, 9(3) pp. 50-57. (English abstract only).

Hsu et al., "Evaluation of chitosan-alginate-hyaluronate complexes modified by an RGD containing protein as tissue engineering scaffolds for cartilage regeneration," Artificial Organs, vol. 28, No. 8, 2004, pp. 693-703.

International Preliminary Report on Patentability for International Application No. PCT/US2015/036894 dated Dec. 26, 2017. (23 pages).

International Search Report and Written Opinion for International Application No. PCT/US2015/036894 dated Dec. 4, 2015. (27 pages).

Ji et al., "Coaxially electrospun core/shell structured poly(L-lactide) acid/chitosan nanofibers for potential drug carrier in tissue engineering", Journal of Biomedical Nanotechnology. Oct. 2013; vol. 9, No. 10, pp. 1672-1678. Retrieved from the Internet. <URL: http://www.pubfacts.com/detail/24015496/Coaxially-electrospun-coreshell-structured-polyL-lactide-acidchitosan-nanofibers-for-potential-drug->. entire document.

Ozturk et al., "Preparation and Characterization of Ciprofloxacin-Loaded Alginate/Chitosan Sponge as a Wound Dressing Material," Journal of Applied Polymer Science, vol. 101, pp. 1602-1609 (2006).

Search Report for Russian Application No. 2018102112. (4 pages).

Suneris. Vetigel. May 21, 2015. [retrieved on Aug. 19, 2015). Retrieved from the Internet. <URL: https://web.archive.org/web/20150521234157/http://www.suneris.co/vetigel/>. entire document.

Wang et al., "Chitosan-Alginate PEC Membrane as a Wound Dressing: Assessment of Incisional Wound Healing," 2002, vol. 63., No. 5, pp. 610-618.

Li, D. et al., "Enhanced Hemostatic Performance of Tranexamic Acid-Loaded Chitosan/Alginate Composite Microparticles," Journal of Biomedicine and Biotechnology, vol. 2012, Article ID 981321, 9 pages (2012).

* cited by examiner

FIG. 3

US 12,016,968 B2

HIGHLY EFFICACIOUS HEMOSTATIC ADHESIVE POLYMER SCAFFOLD

CROSS-REFERENCE TO RELATED APPLICATIONS

This application is a continuation of U.S. patent application Ser. No. 15/739,095, filed Dec. 21, 2017, which is a U.S. National Stage Application under 35 U.S.C. § 371 of International Application No. PCT/US2015/036894, filed Jun. 22, 2015, the contents of which are hereby incorporated by reference in their entireties.

BACKGROUND OF THE INVENTION

Hemostasis is a complex, multi-stage mechanism involving an orchestrated effort on the part of many cell types and scaffold formations to begin production of an initial platelet plug at the site of a wound and then develop a fully mature clot capable of arresting blood flow. Hemostasis is usually divided into three phases: primary hemostasis, the coagulation cascade, and fibrinolysis. Initially, a platelet plug is formed as a response to exposed endothelial cells at a compromised surface, after platelets adhere to collagen fibers surrounding said surface. Exposure to collagen "activates" the platelets, prompting them to release coagulation factors that allow for the coagulation cascade to progress. The process ends in the cleavage of fibrinogen by thrombin to form the foundational material for a clot, known as fibrin.

A notable challenge in the treatment of bleeding wound surfaces is presented by the adhesive properties of the physical barrier component of a given hemostatic device. If sustained blood flow is particularly strong, hemostasis can be disrupted as premature platelet plugs and fibrin clots may be ruptured in the process. This difficulty can be exacerbated if a hemostatic device lacks sufficient adhesion and a partially formed plug or clot disengages prematurely from a wound site. Various hemostatic devices seek to increase adhesive strength by utilizing dry devices to dehydrate the wound site. Such devices retard epithelialization and, in turn, slow wound healing substantially.

It would be advantageous to develop an adhesive hemostatic device that does not limit wound hydration during and after hemostasis.

SUMMARY OF THE INVENTION

The invention is a class of biocompatible polymer compositions useful in facilitating and maintaining hemostasis.

In one embodiment of the invention, the biocompatible polymeric composition comprises (a) one or more than one polyanionic polymer, (b) one or more than one polycationic polymer, and (c) a solvent. In one embodiment of the invention, one polyanionic polymer comprises sodium alginate; in one embodiment of the invention, one polycationic polymer comprises chitosan; in one embodiment of the invention, a solvent comprises water. In a preferred embodiment of the invention the biocompatible polymeric composition comprises sodium alginate, chitosan, and water.

Various properties associated with each component of the biocompatible polymeric compositions may impact the properties of the final product. Properties associated with the selection of a particular polyanionic polymer include chain length, molecular weight, viscosity in solution, particle size, and morphology. Properties associated with the selection of a particular polycationic polymer include chain length, molecular weight, degree of deacetylation, viscosity in solution, particle size, and morphology. Properties associated with the solvent include pH and polarity. Final biocompatible polymer composition properties include viscosity, hemostatic efficiency, fracture strength, and pH.

Factors impacting the properties of the final product include the amount of each component as well as the method of manufacturing.

DETAILED DESCRIPTION OF THE INVENTION

The invention disclosed herein is a class of biocompatible polymer gel compositions useful in facilitating and maintaining hemostasis. The biocompatible polymeric gel composition generally comprises (a) a polyanionic polymer, (b) a polycationic polymer, and (c) a solvent.

Polyanionic Polymer

Preferably the polymeric gel composition comprises about 0.10% to about 5.00% by weight of a polyanionic polymer (or more than one polyanionic polymer). Preferably the polymeric gel composition comprises about 1.00% to about 4.00% by weight of a polyanionic polymer; preferably the polymeric gel composition comprises about 2.00% to about 3.00% by weight of a polyanionic polymer. The polymeric gel composition may comprise about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.05%, about 1.10%, about 1.15%, about 1.20%, about 1.25%, about 1.30%, about 1.35%, about 1.40%, about 1.45%, about 1.50%, about 1.55%, about 1.60%, about 1.65%, about 1.70%, about 1.75%, about 1.80%, about 1.85%, about 1.90%, about 1.95%, about 2.00%, about 2.05%, about 2.10%, about 2.15%, about 2.20%, about 2.25%, about 2.30%, about 2.35%, about 2.40%, about 2.45%, about 2.50%, about 2.55%, about 2.60%, about 2.65%, about 2.70%, about 2.75%, about 2.80%, about 2.85%, about 2.90%, about 2.95%, about 3.00%, about 3.05%, about 3.10%, about 3.15%, about 3.20%, about 3.25%, about 3.30%, about 3.35%, about 3.40%, about 3.45%, about 3.50%, about 3.55%, about 3.60%, about 3.65%, about 3.70%, about 3.75%, about 3.80%, about 3.85%, about 3.90%, about 3.95%, about 4.00%, about 4.05%, about 4.10%, about 4.15%, about 4.20%, about 4.25%, about 4.30%, about 4.35%, about 4.40%, about 4.45%, about 4.50%, about 4.55%, about 4.60%, about 4.65%, about 4.70%, about 4.75%, about 4.80%, about 4.85%, about 4.90%, about 4.95%, or about 5.00% by weight of a polyanionic polymer.

In one embodiment of the invention, the polyanionic polymer may be a polystyrene sulfonate (such as sodium polystyrene sulfonate), a polyacrylate (such as sodium polyacrylate), a polymethacrylate (such as sodium polymethacrylate), a polyvinyl sulphate (such as sodium polyvinyl sulphate), a polyphosphate (such as sodium polyphosphate), Iota carrageenan, Kappa carrageenan, gellan gum, carboxyl methyl cellulose, carboxyl methyl agarose, carboxyl methyl dextran, carboxyl methyl chitin, carboxyl methyl chitosan, a polymer modified with a carboxyl methyl group, an alginate (such as sodium alginate), a polymer containing a plurality of carboxylate groups, a xanthan gum, and combinations thereof. Preferably, the polyanionic polymer is an alginate, more preferably sodium alginate. In one embodiment the polymeric composition comprises about 2.25% alginate by weight; in one embodiment the polymeric composition comprises about 2.50% alginate by weight.

In one embodiment of the invention, the polyanionic polymer has a chain length of between about 1,000 nm and about 3,000 nm. The increased chain length of a particular polyanionic polymer aids in the increased ability of the composition—when applied to a wound—to adhere to tissue. Short-chain polyanionic polymers may yield a biocompatible polymeric gel composition having difficult or poor adhesion to a wound. The polyanionic polymer may have a chain length of about 1,000, about 1,100, about 1,200, about 1,300, about 1,400, about 1,500, about 1,600, about 1,700, about 1,800, about 1,900, about 2,000, about 2,100, about 2,200, about 2,300, about 2,400, about 2,500, about 2,600, about 2,700, about 2,800, about 2,900, or about 3,000 nm.

In one embodiment the polyanionic polymer comprises particles having an average particle size of between 10 mesh and 300 mesh. As the particle size of the polyanionic polymer increases, the amount of cell adhesion to the polymer increases. However as the particle size of the polyanionic polymer increases this may decrease surface area of wound coverage. Preferably the polyanionic polymer comprises particles having an average particle size of between 100 mesh and 270 mesh. Preferably the polyanionic polymer comprises particles having an average particle size of between 120 mesh and 250 mesh. Preferably the polyanionic polymer comprises particles having an average particle size of between 150 mesh and 200 mesh. Preferably the polyanionic polymer comprises particles having an average particle size of about 180 mesh. The polyanionic polymer may have an average particle size of about 80, about 100, about 120, about 150, about 180, about 200, about 250, or about 270 mesh.

In one embodiment the polyanionic polymer has a number average molecular weight (Mn) of between 100 kDa to about 1,000 kDa. Preferably the polyanionic polymer has a molecular weight of between about 500 kDa to about 900 kDa. In a preferred embodiment the polyanionic polymer has a molecular weight of about 800 kDa. Higher molecular weight polyanionic polymers will increase the viscosity of the polymeric gel composition and will maintain its flowability to resist fracture and prevent or reduce blood passage through it. The polyanionic polymer may have a molecular weight of about 100 kDa, about 150 kDa, about 200 kDa, about 250 kDa, about 300 kDa, about 350 kDa, about 400 kDa, about 450 kDa, about 500 kDa, about 550 kDa, about 600 kDa, about 650 kDa, about 700 kDa, about 750 kDa, about 800 kDa, about 850 kDa, about 900 kDa, about 950 kDa, or about 1,000 kDa.

In one embodiment the polyanionic polymer has a viscosity of between about 100 centipoise (cP) to about 2,000 cP in a 1% weight per volume (w/v) solution of water at about 25° C. Preferably the polyanionic polymer has a viscosity of between about 100 cP to about 1,000 cP in a 1% w/v solution of water at about 25° C. The polyanionic polymer may have a viscosity of about 100 cP, about 200 cP, about 300 cP, about 400 cP, about 500 cP, about 600 cP, about 700 cP, about 800 cP, about 900 cP, about 1,000 cP, about 1,100 cP, about 1,200 cP, about 1,300 cP, about 1,400 cP, about 1,500 cP, about 1,600 cP, about 1,700 cP, about 1,800 cP, about 1,900 cP, or about 2,000 cP in a 1% w/v solution of water at about 25° C. Preferably the polyanionic polymer has a viscosity of about 1,000 cP in a 1% w/v solution of water at about 25° C.

The polyanionic polymer present in the polymeric gel composition comprises the scaffold onto which fibrin adheres. The morphology of polyanionic polymer particles is preferably a mesh or combination of fibrous particles onto which fibrin can easily bind and form a patch at the wound bed. The polyanionic polymer particles may have a morphology that is fibrous, crystalline, amorphous, spherical, cuboidal, or a combination thereof.

Polyanionic polymers may be obtained from various commercial suppliers. However, the source of polyanionic polymer can impact the potential for foreign contaminants, such as prions, to be present in raw materials. In one embodiment the polyanionic polymer is obtained from an organic source. In a preferred embodiment the polyanionic polymer is sodium alginate. In one preferred embodiment the sodium alginate is obtained from marine algae such as *Macrocystis pyrifera* (kelp).

Polycationic Polymer

Preferably the polymeric gel composition comprises about 5% to about 40% by weight of a polycationic polymer (or more than one polycationic polymer). Preferably the polymeric gel composition comprises about 8% by weight of a polycationic polymer; preferably the polymeric gel composition comprises about 22% by weight of a polycationic polymer. The polymeric gel composition may comprise about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% by weight of a polycationic polymer.

In one embodiment of the invention, the polycationic polymer may be a chitosan (such as chitosan chloride), chitin, diethylaminoethyl-dextran, diethylaminoethyl-cellulose, diethylaminoethyl-agarose, diethylaminoethyl-alginate, a polymer modified with a diethylaminoethyl group, a polymer containing a plurality of protonated amino groups, and a polypeptide having an average residue isoelectric point above 7, and combinations thereof. Preferably the polycationic polymer is a chitosan; preferably the polycationic polymer is chitosan chloride. Preferably the polycationic polymer is diethylaminoethyl-dextran (DEAE-Dextran).

In one embodiment of the invention, the polycationic polymer has a chain length of between about 2,000 nm and about 4,000 nm. In a preferred embodiment the polycationic polymer has a chain length of between about 2,800 nm and about 2,900 nm. In a preferred embodiment the polycationic polymer has a chain length of between about 2,850 nm. In a preferred embodiment the polycationic polymer has a chain length of between about 2,849 nm. The polyanionic polymer may have a chain length of about 2,000, about 2,100, about 2,200, about 2,300, about 2,400, about 2,500, about 2,600, about 2,700, about 2,800, about 2,900, about 3,000, about 3,100, about 3,200, about 3,300, about 3,400, about 3,500, about 3,600, about 3,700, about 3,800, about 3,900, or about 4,000 nm.

In one embodiment the polycationic polymer comprises particles having an average particle size of between 50 mesh and 500 mesh. As the particle size of the polycationic polymer increases, the amount of cell adhesion to the polymer increases. However as the particle size of the polycationic polymer increases this may decrease surface area of wound coverage. Preferably the polycationic polymer comprises particles having an average particle size of between 60 mesh and 400 mesh. Preferably the polycationic polymer comprises particles having an average particle size of between 80 mesh and 325 mesh. Preferably the polycationic polymer comprises particles having an average particle size of between 80 mesh and 120 mesh. Preferably the polycationic polymer comprises particles having an average particle size of about 100 mesh. The polycationic polymer may have an average particle size of about 50, about 60, about 80, about 100, about 120, about 150, about 180, about 200, about 250, about 270, about 325, about 400, or about 500 mesh.

In one embodiment the polycationic polymer has a number average molecular weight (Mn) of between about 1 kDa to about 2,000 kDa. Preferably the polycationic polymer has a molecular weight of between about 1 kDa to about 1,000 kDa. Preferably the polycationic polymer has a molecular weight of between about 800 kDa to about 1,200 kDa. Preferably the polycationic polymer has a molecular weight of between about 900 kDa to about 1,100 kDa. In a preferred embodiment the polycationic polymer has a molecular weight of about 1,000 kDa. Molecular weight of the polycationic polymer influences its ability to carry charge, and with greater molecular weight comes greater charge density, which in turn positively impacts hemostasis. The polycationic polymer may have a molecular weight of about 100 kDa, about 200 kDa, about 300 kDa, about 400 kDa, about 500 kDa, about 600 kDa, about 700 kDa, about 800 kDa, about 900 kDa, about 1,000 kDa, about 1,100 kDa, about 1,200 kDa, about 1,300 kDa, about 1,400 kDa, about 1,500 kDa, about 1,600 kDa, about 1,700 kDa, about 1,800 kDa, about 1,900 kDa, or about 2,000 kDa.

In one embodiment the polycationic polymer has a viscosity of between about 10 cP to about 1,000 cP in a 1% weight per volume (w/v) solution of 5% acetic acid at about 25° C. Preferably the polycationic polymer has a viscosity of between about 50 cP to about 1,000 cP in a 1% w/v solution of 5% acetic acid at about 25° C. The polycationic polymer may have a viscosity of about 10 cP, about 20 cP, about 30 cP, about 40 cP, about 50 cP, about 60 cP, about 70 cP, about 80 cP, about 90 cP, about 100 cP, about 110 cP, about 120 cP, about 130 cP, about 140 cP, about 150 cP, about 160 cP, about 170 cP, about 180 cP, about 190 cP, about 200 cP, about 210 cP, about 220 cP, about 230 cP, about 240 cP, about 250 cP, about 260 cP, about 270 cP, about 280 cP, about 290 cP, about 300 cP, about 310 cP, about 320 cP, about 330 cP, about 340 cP, about 350 cP, about 360 cP, about 370 cP, about 380 cP, about 390 cP, about 400 cP, about 410 cP, about 420 cP, about 430 cP, about 440 cP, about 450 cP, about 460 cP, about 470 cP, about 480 cP, about 490 cP, about 500 cP, about 510 cP, about 520 cP, about 530 cP, about 540 cP, about 550 cP, about 560 cP, about 570 cP, about 580 cP, about 590 cP, about 600 cP, about 610 cP, about 620 cP, about 630 cP, about 640 cP, about 650 cP, about 660 cP, about 670 cP, about 680 cP, about 690 cP, about 700 cP, about 710 cP, about 720 cP, about 730 cP, about 740 cP, about 750 cP, about 760 cP, about 770 cP, about 780 cP, about 790 cP, about 800 cP, about 810 cP, about 820 cP, about 830 cP, about 840 cP, about 850 cP, about 860 cP, about 870 cP, about 880 cP, about 890 cP, about 900 cP, about 910 cP, about 920 cP, about 930 cP, about 940 cP, about 950 cP, about 960 cP, about 970 cP, about 980 cP, about 990 cP, or about 1,000 cP in a 1% w/v solution of 5% acetic acid at about 25° C. Preferably the polycationic polymer has a viscosity of about 80 cP in a 1% w/v 5% acetic acid solution at about 25° C.

The polycationic polymer particles present in the polymeric gel composition comprise a surface onto which cells may adhere to permit platelet aggregation. A greater surface area of polycationic polymer particles may accelerate hemostasis. The morphology of polycationic polymer particles is preferably spherical with pores and allows for aggregation both inside the particle as well as outside. The polycationic polymer particles may have a morphology that is fibrous, crystalline, amorphous, spherical, cuboidal, or a combination thereof.

The polycationic polymer may also be bound or functionalized to a core of a different material such as a polymeric substance. In one embodiment the core is an inert core. In one embodiment the core is poly-L-lactic acid. Binding the polycationic polymer to a core may, for example, reduce the amount of polycationic polymer needed to achieve a given surface area compared with a solid particle of a given polycationic polymer. Binding the polycationic polymer to a core may also allow for a geometries that would otherwise be impossible or impractical absent the core. In one embodiment a cuboidal core is coated in chitosan to yield a cuboidal geometry for chitosan—where chitosan on its own will not form cuboidal geometries under ordinary conditions. Binding the polycationic polymer to a core may also permit a polycationic polymer to exist in a crystalline form within the biocompatible polymer gel composition when such polymer would not otherwise be able to exist as a crystal based on the conditions in the composition. In one embodiment a core of poly-L-lactic acid is bound to diethylaminoethyl-dextran (DEAE-Dextran) and used in a stable biocompatible polymer gel composition comprising alginate—where DEAE-Dextran cannot form a crystal on its own under ordinary conditions and may not form a stable gel when used with alginate alone. In a preferred embodiment the one or more than one polycationic polymer comprises diethylaminoethyl-dextran bound as a coating to a core of poly-L-lactic acid; the one or more than one polycationic polymer comprises diethylaminoethyl-dextran covalently linked to a core of poly-L-lactic acid.

Polycationic polymers may be obtained from various commercial suppliers. However, the source of polycationic polymer can impact the potential for foreign contaminants, such as prions, to be present in raw materials. In one embodiment the polycationic polymer is obtained from an organic source. When the polycationic polymer is chitosan, it may be obtained from crustaceans, fungi, insects, and other organisms. Chitosan may also be obtained from plant sources. In one embodiment the chitosan is obtained from algae. In a preferred embodiment the polycationic polymer is chitosan and it is obtained from fungi such as the genus *Pleurotus*. In a preferred embodiment the polycationic polymer is chitosan and it is obtained from marine invertebrates. In one embodiment the polycationic polymer is chitosan and it is obtained from *Aspergillus niger*.

When the polycationic polymer is chitosan, the degree of deacetylation is a factor that impacts the properties of the polymeric gel composition. Chitosan is an analog to the commonly known chitin, and the degree of deacetylation of chitin coincides with hemostatic efficacy. In one embodiment the chitosan has an average degree of deacetylation of between about 75.0% to about 99.5%. Preferably the chitosan has an average degree of deacetylation of between about 75.0% to about 85.0%. Preferably the chitosan has an average degree of deacetylation of between about 78.0% to about 83.0%. Preferably the chitosan has an average degree of deacetylation of between about 80.0% to about 81.0%. Preferably the chitosan has an average degree of deacetylation of 80.5%. The chitosan may have an average degree of deacetylation of about 75.0%, about 75.5%, about 76.0%, about 76.5%, about 77.0%, about 77.5%, about 78.0%, about 78.5%, about 79.0%, about 79.5%, about 80.0%, about 80.5%, about 81.0%, about 81.5%, about 82.0%, about 82.5%, about 83.0%, about 83.5%, about 84.0%, about 84.5%, about 85.0%, about 85.5%, about 86.0%, about 86.5%, about 87.0%, about 87.5%, about 88.0%, about 88.5%, about 89.0%, about 89.5%, about 90.0%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, or about 99.5%.

Solvent

Biocompatible polymeric compositions of the invention contain between about 50.0% to about 90.0% weight of a solvent. Preferably the compositions comprise between about 50.0% to about 90.0% solvent; preferably the compositions comprise between about 60.0% and about 90.0% solvent; preferably the compositions comprise between about 75.0% and about 90.0% solvent. The solvent may be present in the biocompatible polymeric composition in an amount of about 50.0%, about 50.5%, about 51.0%, about 51.5%, about 52.0%, about 52.5%, about 53.0%, about 53.5%, about 54.0%, about 54.5%, about 55.0%, about 55.5%, about 56.0%, about 56.5%, about 57.0%, about 57.5%, about 58.0%, about 58.5%, about 59.0%, about 59.5%, about 60.0%, about 60.5%, about 61.0%, about 61.5%, about 62.0%, about 62.5%, about 63.0%, about 63.5%, about 64.0%, about 64.5%, about 65.0%, about 65.5%, about 66.0%, about 66.5%, about 67.0%, about 67.5%, about 68.0%, about 68.5%, about 69.0%, about 69.5%, about 70.0%, about 70.5%, about 71.0%, about 71.5%, about 72.0%, about 72.5%, about 73.0%, about 73.5%, about 74.0%, about 74.5%, about 75.0%, about 75.5%, about 76.0%, about 76.5%, about 77.0%, about 77.5%, about 78.0%, about 78.5%, about 79.0%, about 79.5%, about 80.0%, about 80.5%, about 81.0%, about 81.5%, about 82.0%, about 82.5%, about 83.0%, about 83.5%, about 84.0%, about 84.5%, about 85.0%, about 85.5%, about 86.0%, about 86.5%, about 87.0%, about 87.5%, about 88.0%, about 88.5%, about 89.0%, about 89.5%, about 90.0%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, or about 99.5%.

Non-limiting examples of solvents include water, ethanol, amyl acetate, acetone, methyl ethyl ketone, isopropanol, tetrahydrofuran, and combinations thereof. Preferably the solvent is polar. Preferably the solvent is pH neutral (about 7.0). Preferably the solvent is water. Preferably when the solvent is water, the solvent is present in the biocompatible polymeric composition in an amount of about 89.5%. Preferably when the solvent is water, the solvent is present in the biocompatible polymeric composition in an amount of between about 77.0% and about 78.0%.

Biocompatible Polymer Composition

The biocompatible polymeric composition may be a gel that comprises between about 0.1% to about 5% by weight of one or more than one polyanionic polymer, between about 10% to about 40% by weight of one of more than one polycationic polymer; and between about 50% to 99.9% by weight solvent.

In a preferred embodiment the biocompatible polymeric gel composition comprises (a) between about 0.0200 g/mL and about 0.0230 g/mL of one or more than one polyanionic polymer and (b) between about 0.185 g/mL and about 0.210 g/mL of one of more than one polycationic polymer. In a preferred embodiment the biocompatible polymeric gel composition comprises (a) between about 0.0200 g/mL and about 0.0230 g/mL of sodium alginate and (b) between about 0.185 g/mL and about 0.210 g/mL of chitosan. In a preferred embodiment the biocompatible polymeric gel composition comprises about 0.02247 g/mL of one or more than one polyanionic polymer and about 0.200 g/mL of one of more than one polycationic polymer. In a preferred embodiment the biocompatible polymeric gel composition comprises about 0.02247 g/mL of sodium alginate and about 0.200 g/mL of chitosan measured as anhydrous powders. In a preferred embodiment the biocompatible polymeric gel composition comprises about 0.0225 g/mL of sodium alginate and about 0.200 g/mL of chitosan measured as anhydrous powders. In a preferred embodiment the biocompatible polymeric gel composition comprises about 0.0212 g/mL of one or more than one polyanionic polymer and about 0.1887 g/mL of one of more than one polycationic polymer. In a preferred embodiment the biocompatible polymeric gel composition comprises about 0.0212 g/mL of sodium alginate and about 0.1887 g/mL of chitosan measured as anhydrous powders. In a preferred embodiment the biocompatible polymeric gel composition comprises about 0.021 g/mL of sodium alginate and about 0.190 g/mL of chitosan measured as anhydrous powders. A preferred solvent is water.

The inventive biocompatible polymeric gel composition is able to clot blood rapidly while maintaining a strong clot. Clot strength is a primary metric of the utility of a biocompatible polymeric composition. A Sonoclot coagulation analyzer (marketed by Sienco as Sonoclot Analyzer) is recognized as a suitable method for testing efficacy of hemostatic devices. Clot strength of a formed clot increases over time, depending upon the activator it is exposed to. The clot strength of a clot on a wound exposed to an inventive biocompatible polymeric compositions may be 50% higher than the strength of a clot formed without exposure to the inventive composition. In a preferred embodiment the clot strength of a clot on a wound exposed to the inventive biocompatible polymeric compositions is from about 90 to about 200 clot strength units (CSU) at t=15 minutes.

Time to clot is another primary metric of the utility of a biocompatible polymeric composition. Clot strength (and clot strength units) increase over time. Hemostasis of a wound should be achieved rapidly to minimize blood loss. The biocompatible polymeric composition facilitates hemostasis when applied to a wound, and preferably time to clot is achieved in 120 seconds or less, preferably in 90 seconds or less, preferably in 60 seconds or less, preferably 30 seconds or less, preferably 15 seconds or less. The time to clot of a wound exposed to the inventive biocompatible polymeric compositions is about 190% faster than the time to clot of a wound without exposure to the inventive composition. The biocompatible polymeric composition can preferably clot blood in vitro in 120 seconds or less, preferably in 90 seconds or less, preferably in 60 seconds or less, preferably 30 seconds or less, preferably 15 seconds or less. The time to clot blood exposed to the inventive biocompatible polymeric composition (in vitro) is about 190% faster than the time to clot without exposure to the inventive composition (in vitro). In one embodiment about 13 mg or more of the inventive composition coagulates about 0.34 mL of blood in vitro.

Adhesive strength is yet another metric of the utility of a biocompatible polymeric gel composition. The inventive compositions should demonstrate sufficient adhesion to a wound to keep the composition at the site of the wound but without the permanence of adhesives such as cyanoacrylate glues. The biocompatible polymeric composition preferably withstands a vertical strain of up to 0.5 Newtons per square millimeter without fracture between two samples of tissue. In one embodiment, 1 mL of a biocompatible polymeric gel is placed between two pieces of chicken liver (20 mm×20 mm×5 mm) and compressed, and the gel withstands a vertical strain of about 0.5 Newtons per square millimeter without fracture when then the tissue samples are pulled apart vertically.

The biocompatible polymeric gel composition may be characterized by various methods including viscosity, pH, Fourier Transform Infrared (FTIR) spectroscopy, and chemical analysis.

The inventive biocompatible polymeric composition preferably has a viscosity between about 145,000 (centipoise) cP and about 250,000 cP at about 25° C. In a preferred embodiment the biocompatible polymeric composition has a viscosity of between about 165,000 cP and about 174,000 cP at about 25° C. In a preferred embodiment the biocompatible polymeric composition has a viscosity of between about 169,000 cP and about 170,000 cP at about 25° C. In a preferred embodiment the biocompatible polymeric composition has a viscosity of about 169,500 cP at about 25° C. A preferred viscosity allows for maximum adhesion capabilities which, in turn, affects performance. Subtle alterations in viscosity can have a substantial impact on product efficacy. The biocompatible polymeric composition may have a viscosity of about 145,000 cP, about 145,500 cP, about 146,000 cP, about 146,500 cP, about 147,000 cP, about 147,500 cP, about 148,000 cP, about 148,500 cP, about 149,000 cP, about 149,500 cP, about 150,000 cP, about 150,500 cP, about 151,000 cP, about 151,500 cP, about 152,000 cP, about 152,500 cP, about 153,000 cP, about 153,500 cP, about 154,000 cP, about 154,500 cP, 155,000 cP, about 155,500 cP, about 156,000 cP, about 156,500 cP, about 157,000 cP, about 157,500 cP, about 158,000 cP, about 158,500 cP, about 159,000 cP, about 159,500 cP, about 160,000 cP, about 160,500 cP, about 161,000 cP, about 161,500 cP, about 162,000 cP, about 162,500 cP, about 163,000 cP, about 163,500 cP, about 164,000 cP, about 164,500 cP, 165,000 cP, about 165,500 cP, about 166,000 cP, about 166,500 cP, about 167,000 cP, about 167,500 cP, about 168,000 cP, about 168,500 cP, about 169,000 cP, about 169,500 cP, about 170,000 cP, about 170,500 cP, about 171,000 cP, about 171,500 cP, about 172,000 cP, about 172,500 cP, about 173,000 cP, about 173,500 cP, about 174,000 cP, about 174,500 cP, 175,000 cP, about 175,500 cP, about 176,000 cP, about 176,500 cP, about 177,000 cP, about 177,500 cP, about 178,000 cP, about 178,500 cP, about 179,000 cP, about 179,500 cP, about 180,000 cP, about 180,500 cP, about 181,000 cP, about 181,500 cP, about 182,000 cP, about 182,500 cP, about 183,000 cP, about 183,500 cP, about 184,000 cP, about 184,500 cP, about 185,000 cP, about 185,500 cP, about 186,000 cP, about 186,500 cP, about 187,000 cP, about 187,500 cP, about 188,000 cP, about 188,500 cP, about 189,000 cP, about 189,500 cP, about 190,000 cP, about 190,500 cP, about 191,000 cP, about 191,500 cP, about 192,000 cP, about 192,500 cP, about 193,000 cP, about 193,500 cP, about 194,000 cP, about 194,500 cP, 195,000 cP, about 195,500 cP, about 196,000 cP, about 196,500 cP, about 197,000 cP, about 197,500 cP, about 198,000 cP, about 198,500 cP, about 199,000 cP, about 199,500 cP, about 200,000 cP, about 200,500 cP, about 201,000 cP, about 201,500 cP, about 202,000 cP, about 202,500 cP, about 203,000 cP, about 203,500 cP, about 204,000 cP, about 204,500 cP, 205,000 cP, about 205,500 cP, about 206,000 cP, about 206,500 cP, about 207,000 cP, about 207,500 cP, about 208,000 cP, about 208,500 cP, about 209,000 cP, about 209,500 cP, about 210,000 cP, about 210,500 cP, about 211,000 cP, about 211,500 cP, about 212,000 cP, about 212,500 cP, about 213,000 cP, about 213,500 cP, about 214,000 cP, about 214,500 cP, 215,000 cP, about 215,500 cP, about 216,000 cP, about 216,500 cP, about 217,000 cP, about 217,500 cP, about 218,000 cP, about 218,500 cP, about 219,000 cP, about 219,500 cP, about 220,000 cP, about 220,500 cP, about 221,000 cP, about 221,500 cP, about 222,000 cP, about 222,500 cP, about 223,000 cP, about 223,500 cP, about 224,000 cP, about 224,500 cP, 225,000 cP, about 225,500 cP, about 226,000 cP, about 226,500 cP, about 227,000 cP, about 227,500 cP, about 228,000 cP, about 228,500 cP, about 229,000 cP, about 229,500 cP, about 230,000 cP, about 230,500 cP, about 231,000 cP, about 231,500 cP, about 232,000 cP, about 232,500 cP, about 233,000 cP, about 233,500 cP, about 234,000 cP, about 234,500 cP, 235,000 cP, about 235,500 cP, about 236,000 cP, about 236,500 cP, about 237,000 cP, about 237,500 cP, about 238,000 cP, about 238,500 cP, about 239,000 cP, about 239,500 cP, about 240,000 cP, about 240,500 cP, about 241,000 cP, about 241,500 cP, about 242,000 cP, about 242,500 cP, about 243,000 cP, about 243,500 cP, about 244,000 cP, about 244,500 cP, 245,000 cP, about 245,500 cP, about 246,000 cP, about 246,500 cP, about 247,000 cP, about 247,500 cP, about 248,000 cP, about 248,500 cP, about 249,000 cP, about 249,500 cP, or about 250,000 cP at about 25° C.

In a preferred embodiment the polyanionic polymer is sodium alginate having a chain length of between about 1,000 nm and about 3,000 nm, a molecular weight of about 800 kDa, a viscosity of about 1,000 cP in a 1% w/v solution of water at about 25° C., is comprised of particles having an average particle size of about 180 mesh with an amorphous morphology, and is sourced from marine algae.

In a preferred embodiment the polycationic polymer is chitosan having an average degree of deacetylation of about 80.5%, a chain length of between about 2,850 nm, a molecular weight of about 1,000 kDa, a viscosity of between about 80 cP in a 1% w/v solution of 5% acetic acid at about 25° C., is comprised of particles having an average particle size of about 100 mesh with a porous and spherical morphology, and is sourced from marine invertebrates.

In a preferred embodiment the solvent is water.

The inventive biocompatible polymeric composition preferably has a pH between about 6.0 and about 8.0, preferably between about 6.5 and about 7.5, preferably between about 6.8 and about 7.2, preferably about 7.0.

Figure 1:
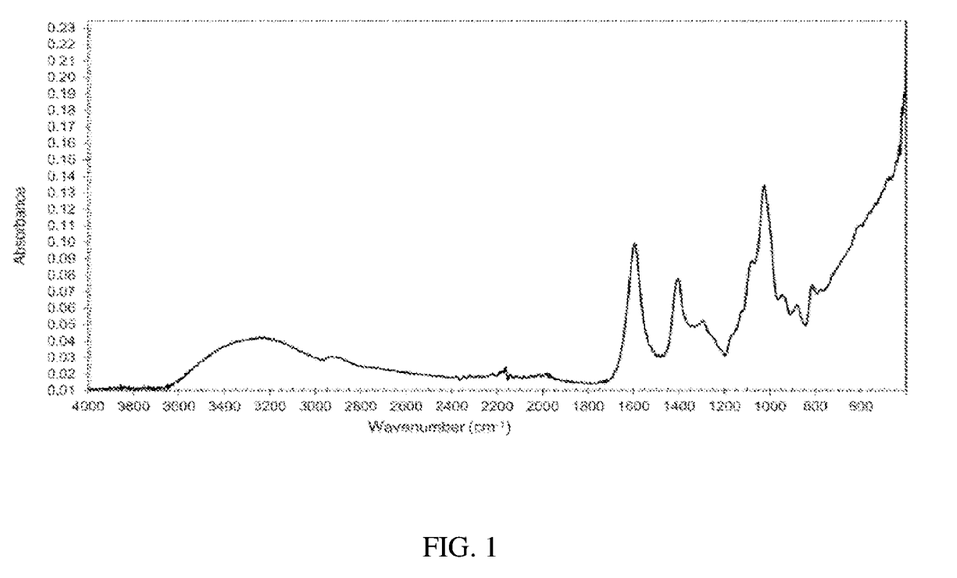
FIG. 1 schematically illustrates a Fourier Transform Infrared spectrum of sodium alginate.
Figure 2:
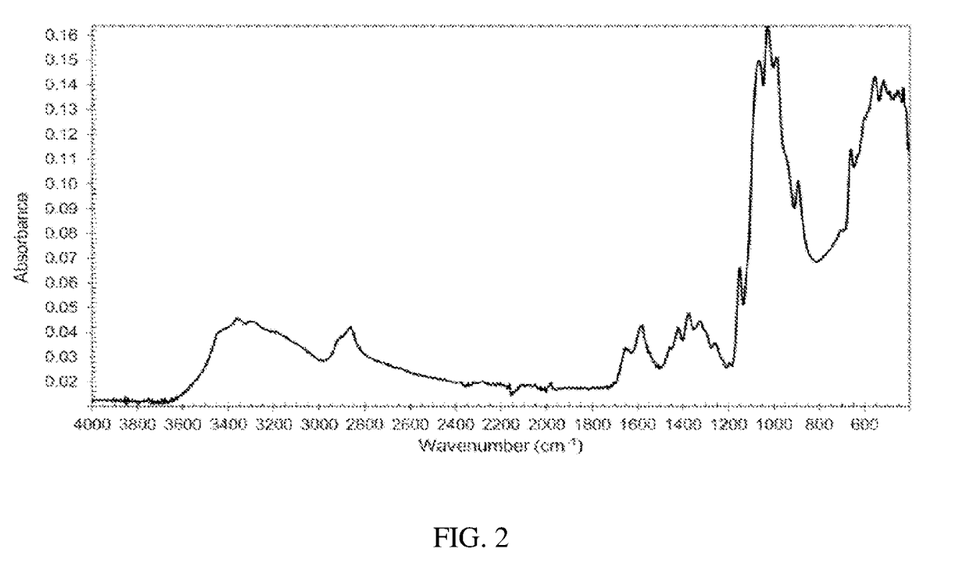
FIG. 2 schematically illustrates a Fourier Transform Infrared spectrum of chitosan.

The FTIR spectra of preferred component alginate and chitosan are shown in FIGS. 1 and 2, respectively. The FTIR spectrum of a preferred biocompatible polymeric gel composition is shown in FIG. 3.

FIG. 1 schematically illustrates a Fourier Transform Infrared spectrum of a preferred sodium alginate. Major absorption peaks appear as follows: a broad peak at from about 3,600 $cm^{-1}$ to about 3,000 $cm^{-1}$ for —OH stretching vibration, at about 2,900 $cm^{-1}$ for C—H stretching vibration, at about 1,600 $cm^{-1}$ for C=O of carboxyl group stretching vibration, at about 1,400 cm$^{-1}$ for carboxyl group stretching vibration overlapped with C—H deformation, and multiple peaks around 1,000 cm$^{-1}$ for C—O vibration corresponding to a polysaccharide structure.

FIG. 2 schematically illustrates a Fourier Transform Infrared spectrum of a preferred chitosan. Absorption peaks appear as follows: a broad peak at from about 3,600 cm$^{-1}$ to about 3,000 cm$^{-1}$ for O—H stretching vibration overlapped to N—H stretching vibration, at about 2,910 cm$^{-1}$ and at about 2,870 cm$^{-1}$ for C—H stretching vibration, at about 1,650 cm$^{-1}$ for C=O of amide stretching vibration, at about 1,580 cm$^{-1}$ for N—H deformation, multiple peaks around 1,400 cm$^{-1}$ for C—H deformation, and multiple peaks around 1,000 cm$^{-1}$ for C—O vibration corresponding to a polysaccharide structure.

Figure 3:
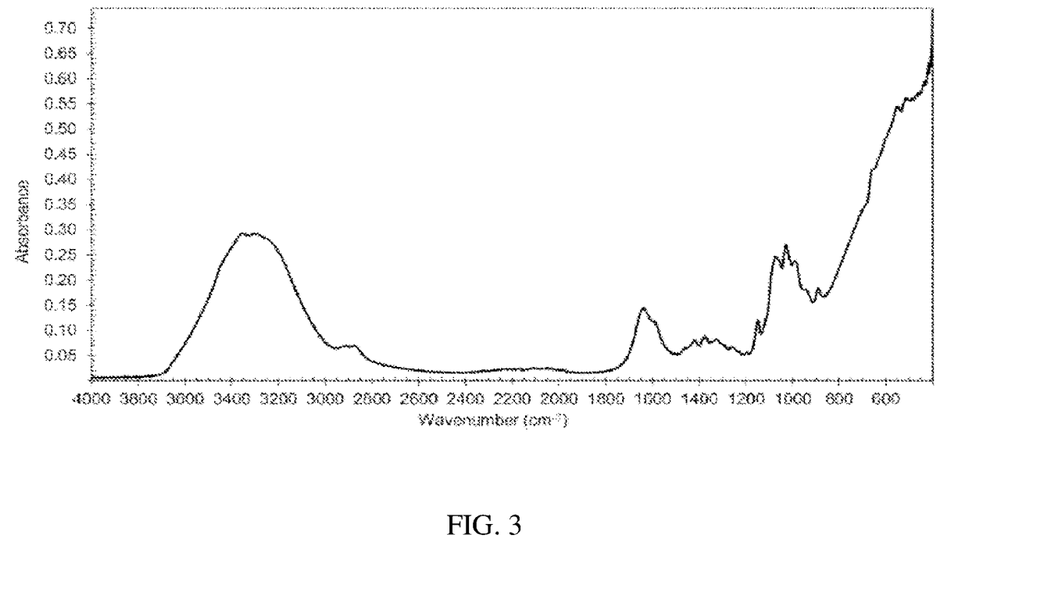
FIG. 3 schematically illustrates a Fourier Transform Infrared spectrum of an inventive biocompatible polymeric composition.

FIG. 3 schematically illustrates a Fourier Transform Infrared spectrum of a preferred biocompatible polymeric composition. Absorption peaks appear as follows: a broad peak at from about 3,600 cm$^{-1}$ to about 3,000 cm$^{-1}$ for O—H stretching vibration overlapped to N—H stretching vibration, at about 2,900 cm$^{-1}$ for C—H stretching vibration, at about 1,640 cm$^{-1}$ for C=O stretching vibration, at about 1,590 cm$^{-1}$ for N—H deformation, multiple peaks around 1,400 cm$^{-1}$ for C—H deformation, and multiple peaks around 1,000 cm$^{-1}$ for C—O vibration corresponding to a polysaccharide structure.

The inventive biocompatible polymeric compositions are intended to be stored at about 25° C. In one embodiment the biocompatible polymeric compositions have a density of between about 1.00 and 1.40 g/mL at about 25° C. In one embodiment the biocompatible polymeric compositions have a density of between about 1.10 and 1.30 g/mL at about 25° C. In one embodiment the biocompatible polymeric compositions have a density of between about 1.20 and 1.22 g/mL at about 25° C. A preferred biocompatible polymeric composition gel has a density of about 1.21 g/mL at about 25° C. The biocompatible polymeric composition may have density of about 1.00 g/mL, about 1.01 g/mL, about 1.02 g/mL, about 1.03 g/mL, about 1.04 g/mL, about 1.05 g/mL, about 1.06 g/mL, about 1.07 g/mL, about 1.08 g/mL, about 1.09 g/mL, about 1.10 g/mL, about 1.11 g/mL, about 1.12 g/mL, about 1.13 g/mL, about 1.14 g/mL, about 1.15 g/mL, about 1.16 g/mL, about 1.17 g/mL, about 1.18 g/mL, about 1.19 g/mL, about 1.20 g/mL, about 1.21 g/mL, about 1.22 g/mL, about 1.23 g/mL, about 1.24 g/mL, about 1.25 g/mL, about 1.26 g/mL, about 1.27 g/mL, about 1.28 g/mL, about 1.29 g/mL, about 1.30 g/mL, about 1.31 g/mL, about 1.32 g/mL, about 1.33 g/mL, about 1.34 g/mL, about 1.35 g/mL, about 1.36 g/mL, about 1.37 g/mL, about 1.38 g/mL, about 1.39 g/mL, or about 1.40 g/mL at about 25° C.

The inventive biocompatible polymeric composition has a modulus of elasticity of between about 6 kPa to about 23 kPa. In one embodiment the biocompatible polymeric composition has a modulus of elasticity of about 16 kPa. The biocompatible polymeric composition may have a modulus of elasticity of about 6 kPa, about 7 kPa, about 8 kPa, about 9 kPa, about 10 kPa, about 11 kPa, about 12 kPa, about 13 kPa, about 14 kPa, about 15 kPa, about 16 kPa, about 17 kPa, about 18 kPa, about 19 kPa, about 20 kPa, about 21 kPa, about 22 kPa, or about 23 kPa.

Preferred storage media containers for the biocompatible polymeric composition include syringes, packets, sachets, tubes, tubs, pumps, bottles, and bags. Preferably the polymeric composition is sterile and suitable for application to humans and animals. One preferred storage media is a 5 mL syringe (sterile); one preferred storage media is a 10 mL syringe (sterile).

The biocompatible polymeric composition may further include optional components such as antimicrobial, preservative, or therapeutic agents. The composition may include silver salts, metal or carbon nanoparticles, antibiotics, hormones, proteins (such as calreticulin, thrombin, prothrombin, Factor VIII), methylparaben, chlorocresol, cetrimide, and iodine, and combinations thereof. In one embodiment the composition further includes iodine. In one embodiment the composition further includes silver nitrate. In one embodiment the composition further includes methylparaben.

Method of Manufacture

Production of the biocompatible polymeric composition generally proceeds as follows. First the one or more polyanionic polymer is mixed with a solvent for a period of time to reach a desired viscosity at about 25° C. The polyanionic mixing may occur between approximately 20 revolutions per minute (RPM) to about 80 RPM, preferably about 48 RPM. Following this first mixing step, the one or more polycationic polymer is added to the mixture and the components are mixed for a period of time to reach a final desired viscosity at about 25° C.; this mixing may occur between approximately 40 RPM to about 100 RPM, preferably about 62 RPM. In a preferred embodiment the mixing in the first mixing period is performed at a lower speed than the mixing in the second mixing period.

In one preferred embodiment sodium alginate is mixed into a vessel with water to reach a desired viscosity at about 25° C. This mixing is performed for about six hours under low-shear mixing, at about 48 RPM. After the sodium alginate and water are mixed, chitosan is added. The mixture including chitosan is mixed under faster mixing than the sodium alginate/water mixing for about one hour at about 25° C. Preferably, upon incorporation of chitosan, the mixing is performed at about 62 RPM.

Preferably, chitosan should not be incorporated simultaneously with the sodium alginate and water as the chitosan particles are porous and tend to pull water out of solution. Simultaneous mixing of all three components (as opposed to first mixing the water and sodium alginate) results in a less efficacious gel that is thicker than desired and may include undissolved sodium alginate. Such gel may comprise a compressible colloid of sodium alginate and wetted chitosan which may exhibit crosslinking issues and poor tissue adherence.

In a preferred embodiment the biocompatible polymeric composition is a colloidal gel with solid particles dispersed in a solution. It is believed that the fluidity of the gel allows for aided wound surface area coverage as it conforms to the site of injury better than solids (such as gauzes or sponges) while the solid particles allow for weight to mechanically prevent bleeding through the fluid, as well as aiding in better cell adhesion/aggregation.

Kit

The packaging of the inventive biocompatible polymeric composition into, for example, a kit or article of manufacture, and application device for any embodiment of the disclosure is chosen and manufactured by persons skilled in the art on the basis of their general knowledge, and adapted according to the nature of the composition to be packaged. Moreover, the type of device to be used may be in particular linked to the consistency of the composition, in particular to its viscosity; it may also depend on the nature of the constituents present in the composition.

The kit or article of manufacture may include, but is not limited to, the inventive composition, a device for the application of the inventive composition, instructions for the use and application of the inventive composition, one or more than one additional solution, a listing of ingredients and/or warnings, and the like. In one embodiment the kit includes a 5 mL syringe filled with an inventive biocompatible polymeric gel along with a separate syringe containing 10% w/v calcium chloride solution in water.

While the present inventions have been illustrated and described in many embodiments of varying scope, it will at once be apparent to those skilled in the art that variations may be made within the spirit and scope of the inventions. Accordingly, it is intended that the scope of the inventions set forth in the appended claims not be limited by any specific wording in the foregoing description, except as expressly provided.

Method of Use

In a primary method of using the inventive polymeric gel, the gel is applied to a wound including, for example, an external laceration, an abrasion, a burn, an ocular laceration, damage to a parenchymal organ, an internal laceration, a laceration in the gastrointestinal tract, superficial cuts and scrapes, internal bleeding, an arterial bleed, a venous bleed, dental or oral bleeds and incisions. The inventive polymeric gel is useful for treating various wounds including those caused unintentionally (such as accidents or unforeseen injuries) as well as those caused intentionally (such as in surgery).

In a primary method of using the inventive polymeric gel, the gel is applied directly to a bleeding wound surface. When applied to a volume of blood, the gel will aid in the clotting of blood at the gel-blood interface. When applying the product, efficacy may decrease if gel is not directly in contact with a bleeding wound surface, though is relatively close to the wound site. The operator may preferentially employ a large-bore syringe in order to rapidly apply a substantial amount of gel, due to the gel's viscous nature. The gel may be dispensed via catheter (such as a 16 gauge or larger) during laparoscopic procedures. In another embodiment, the inventive polymeric gel may be dispensed across a gauze pad to increase the surface area of exposed gel for treatment of large surface bleeds.

Subjects that can benefit from wound treatment using the polymeric compositions of the invention include a variety of animals including humans, mammals such as horses, sheep, cattle, hogs, dogs, cats, and marine animals such as whales, dolphins, seals, otters, fish, and reptiles such as turtles.

After application of the composition to a wound, the composition may be cross-linked by addition of a di- or higher valent cation. Addition of the di- or higher valent cation may assist with removal of the product from the wound site. The di- or higher valent cation may be one or more of $Ca^{2+}$, $Fe^{2+}$, $Fe^{3+}$, $Ag^{2+}$, $Ag^{3+}$, $Au^{2+}$, $Au^{3+}$, $Mg^{2+}$, $Cu^{2+}$, $Cu^{3+}$, and $Zn^{2+}$. In one embodiment of the invention, the cation is $Ca^{2+}$. In a preferred embodiment the di- or higher valent cation is delivered in a solution. The di- or higher valent cation may be present in solution from about 0.1% to about 30% w/v. Preferably the solvent is water. In a preferred embodiment a 10% w/v calcium chloride solution in water may be used.

EXAMPLE

In one form of producing a biocompatible gel, an operator received a beaker, a stirring rod, 106 mL of water, 2.247 g of sodium alginate, and 20 g of chitosan. The 106 mL of water was added to the beaker. Slowly, the operator added up to 50 mg at a time of sodium alginate, followed by 2 minutes of aggressive hand-stirring. This occurred until all sodium alginate was incorporated and was dissolved into the water. The sodium alginate and water solution was left to sit for less than 6 hours to ensure full dissolving. Upon identification of full dissolution, the operator slowly added up to 50 mg at a time of chitosan, followed by 2 minutes of aggressive hand-stirring. This occurred until all chitosan was incorporated and the solution was evenly mixed.

What is claimed is:

1. A polymeric composition comprising:
   a. about 50% to about 94% by weight of water;
   b. about 1% to about 5% by weight of sodium alginate having a molecular weight between about 500 kDa and about 900 kDa dissolved in a solvent to form a solution, wherein the solvent is water; and
   c. about 5% to about 40% by weight of solid chitosan particles having an average particle size between about 50 mesh and about 500 mesh and an average degree of deacetylation of between about 75.0% to about 99.0%;
   wherein the solid chitosan particles are dispersed in the solution of the sodium alginate to form the polymeric composition.

2. The polymeric composition of claim 1, wherein the composition exhibits hemostatic efficacy in vitro in less than about 30 seconds upon introduction to blood.

3. The polymeric composition of claim 1, wherein said chitosan has an average degree of deacetylation of between about 80.0% to about 99.0%.

4. The polymeric composition of claim 1, having a density of between about 1.10 g/mL and about 1.30 g/mL at about 25° C.

5. The polymeric composition of claim 1, wherein about 13 mg or more of said composition coagulates about 0.34 mL of blood in vitro.

6. The polymeric composition of claim 1, having a modulus of elasticity of about 16 kPa.

7. The polymeric composition of claim 1, comprising:
   a. about 2% to about 5% by weight of sodium alginate;
   b. about 8% to about 22% by weight of chitosan; and
   c. about 60% to about 88% by weight of a solvent, wherein the solvent is water.

8. The polymeric composition of claim 7, comprising:
   a. about 3% to about 5% by weight of sodium alginate;
   b. about 10%, about 11%, about 12%, about 13%, about 14%, about 15%, about 16%, about 17%, about 18%, about 19%, or about 20% by weight of chitosan; and
   c. about 60% to about 88% by weight of a solvent, wherein the solvent is water.

9. The polymeric composition of claim 8, comprising:
   a. about 2% to about 3% by weight of sodium alginate;
   b. about 15% to about 22% by weight of chitosan; and
   c. about 70% to about 83% by weight water.

10. The polymeric composition of claim 1, comprising:
    a. about 2% to about 3% by weight of sodium alginate;
    b. about 16% to about 20% by weight of chitosan; and
    c. about 75% to about 80% by weight of a solvent, wherein the solvent is water.

11. The polymeric composition of claim 1, wherein polymeric composition withstands a vertical strain of up to 0.5 Newtons per square millimeter.

12. A method of making a polymeric composition of claim 1, comprising:
    a. mixing sodium alginate having a molecular weight between about 500 kDa and about 900 kDa in a solvent to dissolve the sodium alginate to form a solution, wherein the solvent is water, and
    b. dispersing solid particles of chitosan having an average size between about 50 mesh and about 500 mesh and an average degree of deacetylation between about 75% to about 99.0% to the solution of sodium alginate to form the polymeric composition.

13. A method of facilitating and maintaining hemostasis in a subject comprising applying the polymeric composition of claim 1 at a bleed site of the subject.

14. The method of claim 13, wherein the hemostasis comprises stopping an arterial bleed, a venous bleed, a dental bleed or an oral bleed.

15. The method of claim 13, wherein the hemostasis comprises stopping an arterial bleed.

16. The method of claim 13, wherein the hemostasis comprises stopping an venous bleed.

17. The method of claim 13, wherein the subject is a mammal, a marine animal or a reptile.

18. The method of claim 17, wherein the subject is a human.

19. The method of claim 13, wherein the method comprises applying the polymeric composition using a gauze, a catheter or a syringe.

* * * * *